US010648007B2

(12) United States Patent
Fremy et al.

(10) Patent No.: US 10,648,007 B2
(45) Date of Patent: May 12, 2020

(54) METHOD FOR PRODUCING MERCAPTANS BY HYDROGEN-ASSISTED DISULFIDE ENZYME HYDROGENOLYSIS

(71) Applicant: ARKEMA FRANCE, Colombes (FR)

(72) Inventors: Georges Fremy, Sauveterre De Bearn (FR); Arnaud Masselin, Saint Malo (FR); Hugo Brasselet, Vallet (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/764,189

(22) PCT Filed: Sep. 29, 2016

(86) PCT No.: PCT/FR2016/052480
§ 371 (c)(1),
(2) Date: Mar. 28, 2018

(87) PCT Pub. No.: WO2017/055753
PCT Pub. Date: Apr. 6, 2017

(65) Prior Publication Data
US 2018/0273991 A1  Sep. 27, 2018

(30) Foreign Application Priority Data
Sep. 30, 2015 (FR) ...................................... 15 59264

(51) Int. Cl.
*C12P 11/00*    (2006.01)
*C07C 319/06*   (2006.01)

(52) U.S. Cl.
CPC ............ *C12P 11/00* (2013.01); *C07C 319/06* (2013.01); *C12Y 108/01007* (2013.01); *C12Y 112/01* (2013.01)

(58) Field of Classification Search
None
See application file for complete search history.

(56) References Cited

U.S. PATENT DOCUMENTS

| | | | |
|---|---|---|---|
| 4,059,636 A | 11/1977 | Kubicek | |
| 5,493,058 A | 2/1996 | Cadot et al. | |
| 6,639,110 B2 | 10/2003 | Fremy | |
| 7,759,523 B2 | 7/2010 | Redlingshöfer et al. | |
| 8,008,530 B2 | 8/2011 | Redlingshöfer et al. | |
| 8,426,648 B2 | 4/2013 | Barre et al. | |
| 9,562,006 B2 | 2/2017 | Fremy | |
| 2005/0260250 A1 | 11/2005 | Ott | |
| 2007/0015941 A1 | 1/2007 | Brand et al. | |
| 2007/0213564 A1 | 9/2007 | Yang et al. | |
| 2008/0293974 A1 | 11/2008 | Barth et al. | |
| 2010/0094059 A1 | 4/2010 | Yang et al. | |
| 2010/0286448 A1 | 11/2010 | Yang et al. | |
| 2011/0015443 A1 | 1/2011 | Barth et al. | |
| 2019/0055586 A1 | 2/2019 | Fremy et al. | |

FOREIGN PATENT DOCUMENTS

| | | |
|---|---|---|
| EP | 0649837 A1 | 4/1995 |
| JP | H07304730 A | 11/1995 |
| JP | 2018529358 A | 10/2018 |
| RU | 2219168 C2 | 12/2003 |
| WO | 0196290 A1 | 12/2001 |
| WO | 2004096760 A1 | 11/2004 |
| WO | 2005107723 A2 | 11/2005 |
| WO | 2006015668 A1 | 2/2006 |
| WO | 2007028708 A1 | 3/2007 |
| WO | 2008118925 A2 | 10/2008 |
| WO | 2010046607 A1 | 4/2010 |
| WO | 2013092129 A1 | 6/2013 |
| WO | 2014033399 A1 | 3/2014 |

OTHER PUBLICATIONS

Chandrawati, R., et al., "Triggered Cargo Release by Encapsulated Enzymatic Catalysis in Capsosomes", Nano Letters, 11:4958-4963, (2011), pubs.acs.org/NanoLett.
Du et al., "Derivation of Oridonin with Bioreduction-Responsive Disulfide Bond", Chinese Journal of Chemistry, vol. 2, No. 5, May 22, 2014, pp. 448-453.
International Search Report and Written Opinion for International Application No. PCT/FR2016/052480, dated Jan. 17, 2017, 11 pages.
Keire et al., "Kinetics and Equilibria of Thiol/disulfide Interchange Reactions of Selected Biological Thiols and Related Molecules with Oxidized Glutathione", The Journal of Organic Chemistry, vol. 57. No. 1, Jan. 1992, pp. 123-127.
Lui et al., "Oligomeric Hydrogels Self-Assembled from Reduction-Controlled Condensation", Angwe. Chemie International Edition, vol. 54, No. 12, Mar. 16, 2015, pp. 3639-3642.
Millis et al., "Oxidation/reduction potential of Glutathione", The Journal of Organic Chemistry, vol. 58, No. 15, Jan. 1993, pp. 4144-4146.
Stewart et al., "Mycothiol Disulfide Reductase: Solid Phase Synthesis and Evaluation of Alternative Substrate Analogues", Organic & Biomolecular Chemistry, vol. 6, No. 2, Jan. 2008, p. 385.
Szajewski et al., "Rate Constants and Equilibrium Constants for Thiol-disulfide Interchange Reactions Involving Oxidized Glutathione", Journal of the American Chemical Society, vol. 102, No. 6, Mar. 1980, pp. 2011-2025.

*Primary Examiner* — Anand U Desai
(74) *Attorney, Agent, or Firm* — RatnerPrestia

(57) ABSTRACT

Provided is an enzymatic process for the preparation of a mercaptan of formula R—SH from disulfides utilizing hydrogen.

16 Claims, 1 Drawing Sheet

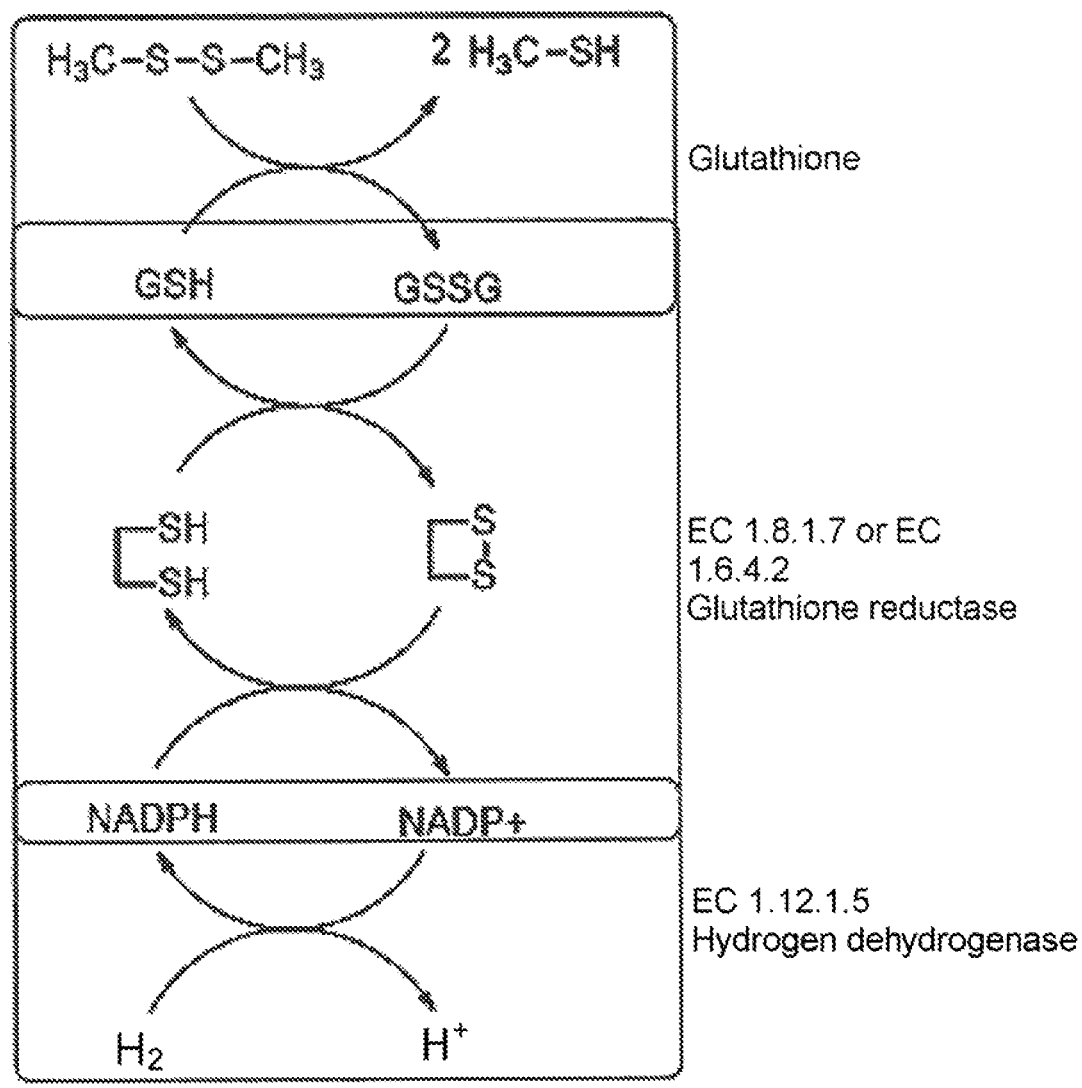

METHOD FOR PRODUCING MERCAPTANS BY HYDROGEN-ASSISTED DISULFIDE ENZYME HYDROGENOLYSIS

CROSS-REFERENCE TO RELATED APPLICATIONS

This is the national phase of International Application Na. PCT/FR2016/052480, filed 29 Sep. 2016, which claims priority to French Application No. 1559264, filed 30 Sep. 2015. The disclosure of each of these applications is incorporated herein by reference in its entirety for all purposes.

FIELD OF THE INVENTION

The present invention relates to a process for the production by enzymatic catalysis of mercaptans, in particular of methyl mercaptan, from disulfides, in particular dimethyl disulfides, and using hydrogen.

BACKGROUND OF THE INVENTION

Mercaptans are highly useful in very numerous fields, for example as flavourings, odorants for gases, chain transfer agents in polymerisation, starting materials for the pharmaceutical or cosmetic industry, for the synthesis of antioxidants, extreme-pressure or anti-wear additives for lubrication. These examples do not in any way limit the uses of the mercaptans known at present and which can be prepared by virtue of the process of the invention.

In particular, the first of the mercaptans, methyl mercaptan ($CH_3SH$), is very industrially beneficial, in particular as starting material in the synthesis of methionine, an essential amino acid very widely used in animal feed. Methyl mercaptan is also a starting material very widely used for the synthesis of numerous other molecules.

Mercaptans may be synthesised by numerous methods such as the sulfhydration of alcohols, the catalytic or photochemical addition of hydrogen sulfide onto unsaturated organic compounds, the substitution of halides, epoxides or organic carbonates by means of hydrogen sulfide, and others.

In particular, methyl mercaptan is currently produced industrially on the tonne scale from methanol and hydrogen sulfide according to the reaction (1):

$$CH_3OH + H_2S \rightarrow CH_3SH + H_2O \quad (1)$$

These processes have the drawbacks of requiring methanol ($CH_3OH$), of synthesising hydrogen sulfide ($H_2S$, from hydrogen and sulfur for example, which also then requires the synthesis of hydrogen), and give rise to by-products of dimethyl ether ($CH_3OCH_3$), dimethyl sulfide ($CH_3SCH_3$) type, and products of cracking and water, which implies numerous steps for purification of the methyl mercaptan.

By way of examples, the description of processes based on these reactions will be found in patent applications such as WO2013092129, WO2008118925, WO2007028708, WO2006015668 and WO2004096760.

It may prove economically advantageous (to avoid methanol synthesis) to wish to produce methyl mercaptan from carbon monoxide, hydrogen and hydrogen sulfide, according to the following synthesis scheme (2):

$$CO + 2H_2 + H_2S \rightarrow CH_3SH + H_2O \quad (2)$$

However, these processes have the drawbacks of requiring synthesis gas ($CO/H_2$) and therefore carrying out steam reforming of a source of hydrocarbons, having the correct proportions between CO and $H_2$, hence being able to adjust the $CO/H_2$ ratio with what is referred to as the "water-gas shift reaction" ($CO + H_2O \rightarrow CO_2 + H_2$), and synthesising $H_2S$.

These processes also generally lead to large proportions of $CO_2$ as by-product, and also to methane, dimethyl sulfide and water. By way of example, descriptions of these processes will be found in patent applications such as US2010286448, US2010094059, US2008293974, US2007213564.

Yet other processes have been described, and combine different reactions such as:

Formation of $CS_2$ and $H_2S$ from methane and sulfur (3):

$$CH_4 + 4S \rightarrow CS_2 + 2H_2S \quad (3)$$

Hydrogenation of $CS_2$ (4):

$$CS_2 + 3H_2 \rightarrow CH_3SH + H_2S \quad (4)$$

It is also possible to use the excess $H_2S$ from reactions (3) and (4) in the reaction with methanol (reaction 1) or the reaction with synthesis gas (reaction 2) to further give methyl mercaptan.

These processes obviously combine the drawbacks described for reactions (1) and (2) with the additional difficulty of having excess hydrogen to carry out reaction (4). Descriptions of these processes will be found in patent applications US2011015443, or, more specifically in relation to reaction (4), in application WO2010046607.

Application WO200196290 proposes a process for synthesising methyl mercaptan directly from methane and $H_2S$ with coproduction of hydrogen. This direct reaction between methane and $H_2S$ occurs by means of a pulsed plasma with corona discharge. Since this application does not describe any examples of synthesis, it may appear difficult to imagine a process for the large-scale industrial synthesis of methyl mercaptan with this technology. Moreover, this process requires the synthesis of $H_2S$ if the latter is not available.

For its part, patent application EP0649837 proposes a process for the synthesis of methyl mercaptan by catalytic hydrogenolysis, with transition metal sulfides, of dimethyl disulfide with hydrogen. Although this process is efficient, it requires relatively high temperatures of the order of 200° C. to obtain industrially advantageous levels of productivity.

Those skilled in the art also know that it is possible to prepare methyl mercaptan by acidification of an aqueous solution of sodium methyl mercaptide ($CH_3SNa$). This method has the major drawback of producing large amounts of salts, such as sodium chloride or sodium sulfate, depending on whether hydrochloric acid or sulfuric acid is used. These saline aqueous solutions are often very difficult to treat and the traces of foul-smelling products which remain mean that this method cannot be readily envisaged on the industrial scale.

The processes for synthesising mercaptans higher than methyl mercaptan also have numerous drawbacks. Thus, the substitution of alcohols with hydrogen sulfide requires high temperatures, and often pressures, and leads to undesired by-products of olefin, ether and sulfide type.

The catalytic or photochemical addition of hydrogen sulfide onto unsaturated compounds often occurs under slightly milder conditions than above, but also leads to numerous by-products formed by isomerisation of the starting material, by non-regioselective addition or by double addition which gives sulfides. Finally, the substitution of halogenated derivatives gives rise to processes which generate large amounts of effluents and saline waste which are not easily reconcilable with industrial processes.

SUMMARY OF THE INVENTION

The subject of the present invention is to propose a novel process for preparing mercaptans, in particular methyl mercaptan, which does not have the drawbacks described in the processes known from the prior art laid out above.

More particularly, a first subject-matter of the present invention is the process for the preparation of a mercaptan of formula R—SH, comprising at least the steps of:
  a) preparation of a mixture comprising:
    1) a disulfide of formula R—S—S—R',
    2) a catalytic amount of amino acid bearing a thiol group or of a thiol-group-containing peptide,
    3) a catalytic amount of an enzyme catalysing the reduction of the disulfide bridge created between two equivalents of said amino acid bearing a thiol group or of said thiol-group-containing peptide,
    4) a catalytic amount of an enzyme catalysing the reduction of hydrogen,
    5) a catalytic amount of a cofactor common to the two enzymes catalysing the reduction and the dehydrogenation,
  b) addition of hydrogen,
  c) carrying out the enzymatic reaction,
  d) recovery of the mercaptan of formula R—SH and the mercaptan of formula R'—SH,
  e) separation and optional purification of the mercaptan of formula R—SH and/or of the mercaptan of formula R'—SH.

BRIEF DESCRIPTION OF THE FIGURE

FIGURE: Reduction with the glutathione/glutathione reductase complex generated by the hydrogen.

DETAILED DESCRIPTION OF THE INVENTION

The enzyme catalysing the reduction of hydrogen may be of any type known to those skilled in the art and for example the enzyme hydrogen dehydrogenase.

Generally speaking, the enzyme catalysing the reduction of the disulfide bridge created between two equivalents of said amino acid bearing a thiol group or of said thiol-group-containing peptide is a reductase enzyme. The term "reductase" is used in the remainder of the description for the explanation of the present invention.

Among the cofactors common to the two enzymes catalysing the reduction and the dehydrogenation (the reductase and the dehydrogenase), mention may be made, by way of nonlimiting examples, of flavinic cofactors and nicotinic cofactors. Preference is given to using nicotinic cofactors and more particularly nicotinamide adenine dinucleotide (NAD), or better still nicotinamide adenine dinucleotide phosphate (NADPH). The cofactors listed above are advantageously used in their reduced forms (for example NADPH, H$^+$) and/or their oxidised forms (for example NADP$^+$), that is to say that they may be added in these reduced and/or oxidised forms into the reaction medium.

In one embodiment of the invention, the amino acid bearing a thiol group and/or the peptide bearing a thiol group may be in the form of the disulfide of said amino acid and/or of said peptide, respectively (for example glutathione in the form of glutathione disulfide).

The organisation and the order of the additions of the different components of steps a) and b) of the process defined above may be carried out in different ways. In any case, the enzymatic reaction of step c) is triggered by the addition of one of the components of the catalytic system: either an enzyme, or one of the compounds added in a stoichiometric amount (disulfide or hydrogen), or one of the compounds added in a catalytic amount (amino acid bearing a thiol group or thiol-group-containing peptide or disulfide corresponding to said molecules or else the cofactor).

More particularly still, the subject of the present invention is the process for the preparation of a mercaptan of formula R—SH, comprising at least the steps of:
  a') preparation of a mixture comprising:
    a disulfide of formula R—S—S—R',
    a catalytic amount of amino acid bearing a thiol group or of a thiol-group-containing peptide,
    a catalytic amount of reductase enzyme corresponding to said amino acid bearing a thiol group or to said thiol-group-containing peptide,
    a catalytic amount of NADPH,
  b') addition of hydrogen with a catalytic amount of hydrogen dehydrogenase enzyme,
  c') carrying out the enzymatic reaction,
  d') recovery of the mercaptan of formula R—SH and of the mercaptan of formula R'—SH,
  e') separation and optional purification of the mercaptan of formula R—SH and of the mercaptan of formula R'—SH.

Within the context of the present invention, any disulfide corresponding to the general formula R—S—S—R' may be involved in the process for producing mercaptan. In the general formula R—S—S—R', R and R', which are identical or different, represent independently of one another a linear, branched or cyclic hydrocarbon-based radical comprising from 1 to 20 carbon atoms, said chain being saturated or bearing one or more unsaturations in the form of double or triple bond(s). R and R' may also form together, and with the sulfur atoms bearing them, a cyclic molecule comprising from 4 to 22 atoms, preferably from 5 to 10 atoms.

According to a preferred aspect, the radicals R and R', which are identical or different, are chosen independently of one another from linear or branched, saturated or unsaturated alkyl, cycloalkyl, aryl, alkylaryl or arylalkyl radicals comprising from 1 to 20 carbon atoms, preferably from 1 to 12 carbon atoms, more preferably still from 1 to 6 carbon atoms and optionally functionalised by one or more functions chosen, nonlimitingly and by way of example, from alcohol, aldehyde, ketone, acid, amide, nitrile or ester functions or else functions bearing sulfur, phosphorus, silicon or halogen.

The disulfide of formula R—S—S—R' is able to be reduced, according to the process of the invention, to mercaptan of formula R—SH and mercaptan of formula R'—SH. When R is different to R', reference is made to asymmetrical disulfides, and when R and R' are identical, reference is made to symmetrical disulfides. In the case of symmetrical disulfides R—S—S—R, the process of the invention leads to a mercaptan of formula R—SH. According to a particularly preferred aspect of the invention, dimethyl disulfide (DMDS) is used with the aim of producing methyl mercaptan CH$_3$SH.

In the case of asymmetrical disulfides R—S—S—R', the process of the invention leads to a mixture of mercaptans of formulae R—SH and R'—SH, which may either be used as is or else subjected to one or more separation operations well known to those skilled in the art, for example distillation.

It is also possible to use, in the process of the invention, mixtures of one or more symmetrical and/or asymmetrical disulfides. Possible mixtures of disulfides may comprise DSOs (disulfide oils), said DSOs thus finding a highly advantageous possibility of exploitation.

According to the process of the invention, the mercaptan(s) produced are generally recovered in the form of a solid, a liquid and/or a gas.

The production process according to the invention is based on the enzymatic reduction of disulfides, in particular dimethyl disulfide, with hydrogen according to the following reaction, illustrated with dimethyl disulfide leading to methyl mercaptan:

$$CH_3SSCH_3 + H_2 \rightarrow 2CH_3SH$$

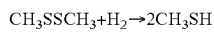

It has now been discovered that this reaction is readily catalysed by the enzymatic system employing a thiol-group-containing amino acid or a thiol-group-containing peptide, for example glutathione, in the form of an (amino acid or peptide)/corresponding reductase enzyme complex, regenerated by the hydrogen, as described in the appended FIG. 1.

Thus, according to the illustration in FIG. 1, the peptide (the example represented being "glutathione") reduces the disulfide ("DMDS" represented) to mercaptan ("methyl mercaptan" represented) by converting into a peptide with a disulfide bridge ("glutathione disulphide" represented). The reductase enzyme ("glutathione reductase" represented, EC 1.8.1.7 or EC 1.6.4.2) regenerates the peptide (glutathione) and this same enzyme is regenerated by a redox enzymatic complex well known to those skilled in the art, for example the NADPH/NADP+ (nicotinamide adenine dinucleotide phosphate (reduced form and oxidised form)) complex. NADP+ is in turn regenerated to NADPH by means of the "hydrogen dehydrogenase" enzyme (EC 1.12.1.5) by virtue of hydrogen. The proton released by the hydrogen does not accumulate as it reacts with the glutathione reductase which gave HS—R—S⁻ after reaction with NADPH and the mercaptide function becomes a mercaptan function.

In other words, the peptide ("glutathione" represented) reduces the disulfide ("DMDS" represented) to mercaptan ("methyl mercaptan" represented) by converting into a peptide with a disulfide bridge ("glutathione disulfide" represented). The enzyme catalysing the reduction ("glutathione reductase" represented, with the example enzyme classification numbers EC 1.8.1.7 or EC 1.6.4.2) regenerates the peptide ("glutathione") while oxidising the cofactor ("NADPH,H⁺" represented). The oxidised form ("NADP⁺" represented) is then reduced by means of a "recycling" redox enzymatic complex well known to those skilled in the art and comprising the dehydrogenase enzyme involved ("hydrogen dehydrogenase" represented with the example enzyme classification number EC 1.1.1.47) and hydrogen. The proton released by the hydrogen does not accumulate because it reacts directly with the mercaptide function formed during the reaction catalysed by the reductase enzyme used.

According to a most particularly suited embodiment, the glutathione/glutathione disulfide system combined with the glutathione reductase enzyme makes it possible according to the present invention to reduced the DMDS to methyl mercaptan.

Glutathione is a tripeptide widely used in biology. In reduced form (glutathione) or oxidised form (glutathione disulfide), this species forms an important redox couple in cells. Thus, glutathione is vital for eliminating heavy metals from organisms. For example, application WO05107723 describes a formulation in which glutathione is used to form a chelating preparation and U.S. Pat. No. 4,657,856 teaches that glutathione also makes it possible to break down peroxides such as $H_2O_2$ into $H_2O$ via glutathione peroxidase. Finally, glutathione also makes it possible to reduce disulfide bridges present in proteins (Rona Chandrawati, "Triggered Cargo Release by Encapsulated Enzymatic Catalysis in Capsosomes", *Nano Lett.*, (2011), vol. 11, 4958-4963).

According to the process of the invention, a catalytic amount of amino acid bearing a thiol group or of a thiol-group-containing peptide is used to produce mercaptans from disulfides.

Among the amino acids bearing a thiol group which may be used in the process of the present invention, mention may be made by way of nonlimiting examples of cysteine and homocysteine. In these cases, the redox enzymatic systems used to regenerate the catalytic cycle in the same way are in these cases the system cysteinelcystine reductase EC 1.8.1.6 and homocysteine/homocysteine reductase.

Among the peptides bearing a thiol group which may be used in the process of the present invention, mention may be made by way of nonlimiting examples of glutathione and thioredoxin. The glutathione/glutathione reductase system described above may thus be replaced by the thioredoxin (CAS No. 52500-60-4)/thioredoxin reductase (EC 1.8.1.9 or EC 1.6.4.5) system.

Glutathione and the glutathione/glutathione reductase system are most particularly preferred for the present invention, due to the costs of these compounds and the ease with which they are procured.

In the process according to the invention, the hydrogen can be added to the reaction medium according to any means known to those skilled in the art, for example via bubbling into the reaction medium, which is advantageously an aqueous-organic reaction medium. The hydrogen pressure in the reactor corresponds to the pressure of the reaction medium itself which is defined hereinafter.

The enzyme used is the hydrogen dehydrogenase enzyme, which is also well known to those skilled in the art.

In the process according to the invention, only the disulfide(s) and the hydrogen are used in a stoichiometric amount and all the other components (amino acid or peptide, cofactor (for example NADPH) and the 2 enzymes) are used in catalytic amounts.

The advantages brought about by the process of the invention are numerous. Among these advantages, mention may be made of the possibility of working in aqueous or aqueous-organic solution, under very mild temperature and pressure conditions and under pH conditions close to neutrality. All these conditions are typical of a "green" or "sustainable" biocatalytic process.

Another advantage when the process uses dimethyl disulfide is that the methyl mercaptan produced, which is in the gaseous state under the reaction conditions, leaves the reaction medium as it is formed, optionally accompanied by any unreacted hydrogen. The methyl mercaptan may therefore be directly used, upon leaving the reactor, in an application further downstream, if the unreacted hydrogen does not adversely affect the latter. In the opposite case, those skilled in the art would easily be able to separate the unconverted hydrogen from the methyl mercaptan. It can also be readily liquefied cryogenically for example, if it is desired to isolate it.

The dimethyl disulfide (DMDS) may be produced at another site from methyl mercaptan and an oxidiser such as oxygen, sulfur or aqueous hydrogen peroxide solution, for example, or else from dimethyl sulfate and sodium disulfide. The DMDS may also originate from a source of disulfide oils (DSO), as indicated above, then be purified for example by reactive distillation as described in application WO2014033399. It should be noted that the DSOs may also be used as is, without the necessity for purification between the different disulfides composing them. A mixture of mercaptans is then obtained by applying the process of the invention.

When DMDS is used as disulfide, the process according to the invention is can then be considered as a process which makes it possible to avoid transporting methyl mercaptan from its site of production by existing industrial routes, to its site of use, if they are different. Indeed, methyl mercaptan is a toxic and extremely foul-smelling gas at room temperature, which significantly complicates its transportation, which is already heavily regulated unlike DMDS. The process described in the present invention can therefore be used to produce methyl mercaptan directly on the site of use of the latter.

Since the DMDS is consumed in the reaction and the methyl mercaptan leaves the reaction medium as it is formed, without hydrogen, or with unconverted hydrogen, no product accumulates in the reaction medium, if it is assumed that hydrogen and DMDS are fed continuously. It is therefore unnecessary to recycle the catalytic system in light of the products entering and leaving the reactor.

In the case of other disulfides, depending on the boiling point of the mercaptan formed and its solubility in the reaction medium, the mercaptan may optionally settle out of the reaction medium, in order to be easily separated, according to techniques well known to those skilled in the art. In the opposite case it can be isolated from the reaction medium, also by any means known to those skilled in the art.

Generally, the reaction temperature is within a range extending from 10° C. to 50° C., preferably between 15° C. and 45° C., more preferably between 20° C. and 40° C.

The pH of the reaction may be between 6 and 8.5, preferably between 7.0 and 8.0. The pH of the reaction medium may be adjusted by means of a buffer. Entirely preferably, the pH of a buffered medium will be chosen at a pH value of between 7.5 and 8.0.

The pressure used for the reaction may range from a reduced pressure compared to atmospheric pressure to several bar (several hundred kPa), depending on the reagents and equipment used. Preferably, use will be made of a pressure ranging from atmospheric pressure to 20 bar (2 MPa) and even more preferably the process will be carried out under a pressure ranging from atmospheric pressure to 3 bar (300 kPa).

The process according to the invention can be carried out batchwise or continuously, in a glass or metal reactor depending on the operating conditions selected and the reagents used. Preferably, a semi-continuous process in which the hydrogen is added as it is consumed in the reaction is chosen.

The ideal hydrogen/disulfide molar ratio is stoichiometry (molar ratio=1) but may vary from 0.01 to 100, if those skilled in the art find any benefit therein, such as continuous addition of the hydrogen while the disulfide is introduced from the start into the reactor. Preferably, this molar ratio is chosen between 1 and 20 overall, over the whole of the reaction.

Any unconverted hydrogen can be recycled from the outlet of the reactor to the inlet of the reactor until it is exhausted completely. Consideration may also be given to a loop with the hydrogen and mercaptan(s) formed, until the hydrogen has completely converted the disulfide(s). As a result, at the end of the reaction when all of the dimethyl disulfide is converted, the outlet gases contain virtually exclusively methyl mercaptan.

The elements present in catalytic amounts in the mixture prepared in step a) above (amino acid bearing a thiol group or a thiol-group-containing peptide, reductase enzyme, cofactor (for example NADPH)) are easily available commercially or can be prepared according to techniques well known to those skilled in the art. These different elements may be in solid or liquid form and may very advantageously be dissolved in water to be used in the process of the invention. The enzymes used may also be grafted onto a support (in the case of supported enzymes).

The aqueous solution of enzymatic complex comprising the amino acid or the peptide may also be reconstituted by methods known to those skilled in the art, for example by permeabilization of cells which contain these elements. This aqueous solution, a composition of which is given in the following Example 1, may be used in contents by weight of between 0.01% and 20% relative to the total weight of the reaction medium. Preferably, a content of between 0.5% and 10% will be used.

According to another aspect, the present invention relates to the use of an aqueous solution of enzymatic complex comprising an amino acid bearing a thiol function as defined above or a peptide bearing a thiol function as defined above, for the synthesis of a mercaptan from a disulfide.

The mixture which may be used for step a) of the process described above, and comprising:
1) a disulfide of formula R—S—S—R',
2) a catalytic amount of amino acid bearing a thiol group or of a thiol-group-containing peptide,
3) a catalytic amount of an enzyme catalysing the reduction of the disulfide bridge created between two equivalents of said amino acid bearing a thiol group or of said thiol-group-containing peptide,
4) optionally a catalytic amount of an enzyme catalysing the reduction of hydrogen,
5) a catalytic amount of a cofactor common to the two enzymes catalysing the reduction and the dehydrogenation,
6) and optionally hydrogen,
where R and R' are as defined above,
is novel and as such forms part of the present invention.

In one embodiment of the invention, the amino acid bearing a thiol group and/or the peptide bearing a thiol group may be in the form of the disulfide of said amino acid and/or of said peptide, respectively. According to yet another embodiment, the cofactor is NADPH in its oxidised form (NADP$^+$) or in its reduced form (NADPH,H$^+$).

More particularly, said mixture comprises:
a disulfide of formula R—S—S—R',
a catalytic amount of amino acid bearing a thiol group or a thiol-group-containing peptide,
a catalytic amount of reductase enzyme corresponding to said amino acid bearing a thiol group or to said thiol-group-containing peptide, and
a catalytic amount of NADPH,
where R and R' are as defined above.

EXAMPLES

The invention will be better understood with the following examples which are nonlimiting relative to the scope of the invention. All the tests presented below were carried out under anaerobic conditions.

Example 1

10 ml of glutathione enzymatic complex are introduced into a reactor containing 150 ml of buffered aqueous solution at pH 7.8. The solution of enzymatic complex contains: 185 mg (0.6 mmol) of glutathione, 200 U of glutathione reductase, 50 mg (0.06 mmol) of NADPH and 200 U of hydrogen dehydrogenase enzyme. The reaction medium is brought to 35° C. with mechanical stirring. A first sample is taken at t=0. Subsequently, the dimethyl disulfide (9.4 g, 0.1 mol) is placed in a burette and added dropwise to the reactor. At the same time, a 4 $L \cdot h^{-1}$ stream of hydrogen (measured under normal temperature and pressure conditions) is introduced into the reactor via bubbling. The reaction is carried out at atmospheric pressure. Gas chromatography analysis of the gases leaving the reactor shows virtually essentially the presence of hydrogen and methyl mercaptan (some traces of water). These outlet gases are trapped in 20% sodium hydroxide in water. The DMDS and the hydrogen (hydrogen/DMDS molar ratio over the whole of the reaction=10.7) are introduced in 6 hours and the reaction is monitored by potentiometric argentometric titration of the methyl mercaptan sodium salt in the trap at the outlet of the reactor. In addition, a final gas chromatography analysis of the reaction medium confirms the absence of DMDS, and of methyl mercaptan which has been driven out of the reactor by the excess hydrogen.

Example 2

To the reaction medium of Example 1, 9.4 g (0.1 mol) of DMDS are reintroduced dropwise in 6 hours, but this time only a 1 $l \cdot h^{-1}$ hydrogen flow is introduced, also over 6 hours (hydrogen/DMDS molar ratio over the whole of the reaction=2.7). The reaction is monitored in the same way as in Example 1, after having changed the 20% sodium hydroxide solution at the outlet of the reactor. The analyses at the end of the reaction confirm the complete disappearance of the DMDS, totally converted into methyl mercaptan found in sodium salt form in the sodium hydroxide solution. Only the gluconolactone is analysed and found in the reaction medium at the end of the reaction. This example shows the robustness of the catalytic system through its reproducibility, and also shows that it is possible to work with hydrogen/DMDS molar ratios which are near to stoichiometry.

Example 3

10 ml of glutathione enzymatic complex are introduced into a reactor containing 70 ml of buffered aqueous solution at pH 6.8. The solution of enzymatic complex contains: 200 mg (0.65 mmol) of glutathione, 500 U of glutathione reductase, 100 mg (0.12 mmol) of NADPH and 50 U of hydrogen dehydrogenase. The latter is obtained from the culture of microorganisms (according to Biller et al., "Fermentation Hyperthermophiler Mikroorganismen am Beispiel von *Pyrococcus Furiosus*", Shaker Verlag, Maastricht/Herzogenrath, 2002), using techniques well known to those skilled in the art.

The reaction medium is brought to 35° C. with mechanical stirring and nitrogen flushing. A first sample is taken at t=0. Subsequently, 20 g (0.22 mol) of dimethyl disulfide are added by means of a syringe.

At the same time, an amount of 4 $l \cdot h^{-1}$ of hydrogen (measured under normal temperature and pressure conditions) is introduced into the reaction medium via bubbling. The reaction is carried out at atmospheric pressure.

Gas chromatography analysis of the gases leaving the reactor shows virtually essentially the presence of hydrogen, nitrogen and and methyl mercaptan (some traces of water). These outlet gases are trapped in sodium hydroxide at 20% by weight in water. The DMDS and the hydrogen (hydrogen/DMDS molar ratio over the whole of the reaction=4.9) are introduced in 6 hours and the reaction is monitored by potentiometric argentometric titration of the methyl mercaptan sodium salt in the trap at the outlet of the reactor.

The final analysis shows that the DMDS has been converted quantitatively into methyl mercaptan. In addition, a final gas chromatography analysis of the reaction medium confirms the absence of DMDS, and of methyl mercaptan which has been driven out of the reactor by the hydrogen.

The invention claimed is:

1. A process for the preparation of a mercaptan of formula R—SH, comprising:
   (a) preparing a mixture, comprising:
      (1) a disulfide of formula R—S—S—R',
      wherein R and R', independently, represent a linear, branched or cyclic hydrocarbon-based radical comprising from 1 to 20 carbon atoms, wherein the hydrocarbon-based radical is saturated or contains one or more unsaturations in the form of double or triple bond(s), or R and R' form together, with the sulfur atoms bearing them, a cyclic group comprising from 4 to 22 atoms,
      (2) a catalytic amount of an amino acid bearing a thiol group or of a thiol-group-containing peptide, wherein the amino acid bearing a thiol group or the thiol-group-containing peptide may optionally be in the form of the corresponding disulfide,
      (3) a catalytic amount of an enzyme catalyzing the reduction of a disulfide bridge created between two equivalents of the amino acid bearing a thiol group or of the thiol-group-containing peptide,
      (4) a catalytic amount of an enzyme catalyzing the reduction of hydrogen, and
      (5) a catalytic amount of a cofactor common to the enzyme catalyzing the reduction of a disulfide bridge created between two equivalents of the amino acid bearing a thiol group or of the thiol-group-containing peptide and the enzyme catalyzing the reduction of hydrogen,
   (b) adding hydrogen with a catalytic amount of a hydrogen dehydrogenase enzyme,
   (c) carrying out the enzymatic reaction,
   (d) recovering the mercaptan of formula R—SH and the mercaptan of formula R'—SH,
   (e) optionally, separating and, optionally, purifying the mercaptan of formula R—SH and/or of the mercaptan of formula R'—SH.

2. The process of claim 1, comprising:
   (a') preparing a mixture, comprising:
      (1) a disulfide of formula R—S—S—R',
      (2) a catalytic amount of amino acid bearing a thiol group or of a thiol-group-containing peptide, wherein the amino acid bearing a thiol group or the thiol-group-containing peptide may optionally be in the form of the corresponding disulfide,
      (3) a catalytic amount of reductase enzyme corresponding to the amino acid bearing a thiol group or to the thiol-group-containing peptide, and
      (5) a catalytic amount of NADPH,
   (b') adding hydrogen with a catalytic amount of hydrogen dehydrogenase enzyme, (c') carrying out the enzymatic reaction,
(d') recovering the mercaptan of formula R—SH and the mercaptan of formula R'—SH,
(e') separating and, optionally, purifiying the mercaptan of formula R—SH and/or of the mercaptan of formula R'—SH.

3. The process of claim 1, wherein R and R', independently, represent a linear, branched or cyclic hydrocarbon-based radical comprising from 1 to 20 carbon atoms, wherein the hydrocarbon-based radical is saturated or contains one or more unsaturations in the form of double or triple bond(s), or R and R' form together, with the sulfur atoms bearing them, a cyclic group comprising from 5 to 10 atoms.

4. The process of claim 1, wherein R and R', independently, represent a linear or branched, saturated or unsaturated alkyl, cycloalkyl, aryl, alkylaryl or arylalkyl radical comprising from 1 to 20 carbon atoms and optionally functionalized by one or more functions chosen from alcohol, aldehyde, ketone, acid, amide, nitrile or ester functions or functions bearing sulfur, phosphorus, silicon or halogen.

5. The process of claim 1, wherein the disulfide of formula R—S—S—R' is dimethyl disulfide.

6. The process of claim 1, wherein the amino acid bearing a thiol group or the peptide bearing a thiol group is chosen from cysteine, homocysteine, glutathione and thioredoxin.

7. The process of claim 1, wherein the hydrogen is introduced into the reaction medium via bubbling.

8. The process of claim 1, wherein the pH of the reaction is between 6 and 8.5.

9. The process of claim 1, wherein the hydrogen/disulfide molar ratio is between 0.01 and 100 over the whole of the reaction.

10. The process of claim 1, wherein the amino acid bearing a thiol group or thiol-group-containing peptide is glutathione.

11. The process of claim 1, wherein the cofactor is a flavinic cofactor or a nicotinic cofactor.

12. The process of claim 1, wherein the cofactor is NADPH.

13. The process of claim 1, wherein
the disulfide of formula R—S—S—R' is dimethyl disulfide,
the amino acid bearing a thiol group or thiol-group-containing peptide is glutathione, and
the cofactor is NADPH.

14. A mixture, comprising:
(1) a disulfide of formula R—S—S—R',
wherein R and R', independently, represent a linear, branched or cyclic hydrocarbon-based radical comprising from 1 to 20 carbon atoms, wherein the hydrocarbon-based radical is saturated or contains one or more unsaturations in the form of double or triple bond(s), or R and R' form together, with the sulfur atoms bearing them, a cyclic group comprising from 4 to 22 atoms,
(2) a catalytic amount of amino acid bearing a thiol group or of a thiol-group-containing peptide, wherein the amino acid bearing a thiol group or the thiol-group-containing peptide may optionally be in the form of the corresponding disulfide,
(3) a catalytic amount of an enzyme catalyzing the reduction of a disulfide bridge created between two equivalents of the amino acid bearing a thiol group or of the thiol-group-containing peptide,
(4) optionally, a catalytic amount of an enzyme catalyzing the reduction of hydrogen,
(5) a catalytic amount of a cofactor common to the enzyme catalyzing the reduction of a disulfide bridge created between two equivalents of the amino acid bearing a thiol group or of the thiol-group-containing peptide and the enzyme catalyzing the reduction of hydrogen, and
(6) optionally, hydrogen.

15. The mixture of claim 14, wherein:
the enzyme catalyzing the reduction of a disulfide bridge created between two equivalents of the amino acid bearing a thiol group or of the thiol-group-containing peptide is a reductase, and
the cofactor is NADPH.

16. The process of claim 1, wherein the enzyme catalyzing the reduction of hydrogen is a hydrogen dehydrogenase.

* * * * *